United States Patent
Kasahara et al.

(10) Patent No.: US 6,703,229 B2
(45) Date of Patent: Mar. 9, 2004

(54) ARYL PROPENAL DOUBLE BOND REDUCTASE

(75) Inventors: Hiroyuki Kasahara, Wako (JP); Laurence B. Davin, Pullman, WA (US); Norman G. Lewis, Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 09/820,096

(22) Filed: Mar. 27, 2001

(65) Prior Publication Data

US 2003/0022168 A1 Jan. 30, 2003

Related U.S. Application Data

(60) Provisional application No. 60/192,266, filed on Mar. 27, 2000.

(51) Int. Cl.[7] .............................. C12N 9/02; C12N 1/20; C12N 15/00; C12N 5/06; C07H 21/04
(52) U.S. Cl. ..................... 435/189; 435/6; 435/252.3; 435/320.1; 435/410; 516/23.2; 516/29.5; 800/295
(58) Field of Search .............................. 435/189, 252.3, 435/320.1, 410, 6; 800/295; 536/23.2, 24.5

(56) References Cited

PUBLICATIONS

Allona, I., et al., "Analysis of Xylen Formation in Pine by cDNA Sequencing," *Proc. Natl. Acad. Sci. USA* 95:9693–9698, Aug. 1998.

Babiychuk, E., et al., "*Arabidopsis thaliana* NADPH Oxidoreductase Homologs Confer Tolerance of Yeasts Toward the Thiol–Oxidizing Drug Diamide," *The Journal of Biological Chemistry* 270 (*44*):26224–26231, Nov. 1995.

Gang, D.R., et al., "Evolution of Plant Defense Mechanisms," *The Journal of Biological Chemistry* 274 (*12*):7516–7526, Mar. 1999.

Nose, M., et al., "Towards the Specification of Consecutive Steps in Macromolecular Lignin Assembly," *Phytochemistry* 39 (*1*):71–79, 1995.

Nucleic Acid Sequence Accession No. AB036735, *EMBL, Sequence Library 'Online!*, Deposited in GenBank on Jan. 14, 2000, Updated Nov. 15, 2001, Hirata, T., et al., "A 38 kDa Allylic Alcohol Dehydrogenase From the Cultured Cells of *Nicotiana tabacum*," 1 pg.

Nucleic Acid Sequence Accession No. BG318152, *EMBL Sequence Database 'Online!*, Deposited in GenBank on Feb. 27, 2001, Sederoff, R., "Molecular Basis of Wood Formation in the Pine Megagenome," 1 pg.

Nucleotide Sequence of Loblolly pine cDNA clone 7C5A, GenBank Accession No. AA556927, GenBank entry created Jul. 30, 1998.

*Primary Examiner*—Ponnathapu Achutamurthy
*Assistant Examiner*—Yong D. Pak
(74) *Attorney, Agent, or Firm*—Christensen O'Connor Johnson Kindness PLLC

(57) ABSTRACT

In one aspect, the present invention provides isolated nucleic acid molecules that each: (a) encode an aryl propenal double bond reductase; and (b) hybridize to a nucleic acid molecule consisting of the complement of the nucleic acid sequence set forth in SEQ ID NO:1 under defined conditions. The present invention also provides isolated aryl propenal double bond reductases. In other aspects, the present invention provides methods of enhancing or inhibiting the expression of aryl propenal double bond reductases in a plant.

22 Claims, No Drawings

SEQUENCE LISTING

```
<160> NUMBER OF SEQ ID NOS: 13

<210> SEQ ID NO 1
<211> LENGTH: 1053
<212> TYPE: DNA
<213> ORGANISM: Pinus Taeda
<220> FEATURE:
<221> NAME/KEY: CDS
<222> LOCATION: (1)..(1053)

<400> SEQUENCE: 1 atg gag cag aga gtt cca aac aga gag cta ata tta gtc gca tat gcc      48
Met Glu Gln Arg Val Pro Asn Arg Glu Leu Ile Leu Val Ala Tyr Ala
1               5                   10                  15 aac gaa ggg ccc gtt aca gat tca cat ttg aat atc aga gaa acc aaa      96
Asn Glu Gly Pro Val Thr Asp Ser His Leu Asn Ile Arg Glu Thr Lys
                20                  25                  30 ctg gat ctt gga agc gtg ggc aaa gat gga tca tct gga gat gtc gct     144
```

```
Leu Asp Leu Gly Ser Val Gly Lys Asp Gly Ser Ser Gly Asp Val Ala
         35                  40                  45 gtg cag aat ctg tgg ata tct gta gat cca tat ctt cgg cag ctt atg        192
Val Gln Asn Leu Trp Ile Ser Val Asp Pro Tyr Leu Arg Gln Leu Met
 50                  55                  60 aag gaa tcc gat gat ggt ctc tat tta cca agt ttt ccg ttg aat cag        240
Lys Glu Ser Asp Asp Gly Leu Tyr Leu Pro Ser Phe Pro Leu Asn Gln
 65                  70                  75                  80 gca atc cga tct att tta gtg ggg aag gta gtg gca tct gct aat ccg        288
Ala Ile Arg Ser Ile Leu Val Gly Lys Val Val Ala Ser Ala Asn Pro
                 85                  90                  95 gcc ttc gaa gtg ggt gat atc gtt tct ggt ttc tat caa gtt tcc gag        336
Ala Phe Glu Val Gly Asp Ile Val Ser Gly Phe Tyr Gln Val Ser Glu
            100                 105                 110 tac gct att gtt cca cga ggc gac ctc atg aaa att gac acc agt gtt        384
Tyr Ala Ile Val Pro Arg Gly Asp Leu Met Lys Ile Asp Thr Ser Val
            115                 120                 125 gtt aaa ccg tct gat tat ttg gga ctt ctg ggg atg ccc gcc ttg act        432
Val Lys Pro Ser Asp Tyr Leu Gly Leu Leu Gly Met Pro Ala Leu Thr
130                 135                 140 gca tgg gct gga ttc ata atc gtc gga gaa cct aaa ccc ggg gat gaa        480
Ala Trp Ala Gly Phe Ile Ile Val Gly Glu Pro Lys Pro Gly Asp Glu
145                 150                 155                 160 gtt ttt gtt tcg gca gca gcg ggc tca gtg gga atg ctg gtt ggg cag        528
Val Phe Val Ser Ala Ala Ala Gly Ser Val Gly Met Leu Val Gly Gln
                165                 170                 175 ctc gcc aaa atc aaa agc tgc cgc gtt gtt ggc agc gca ggt agc gac        576
Leu Ala Lys Ile Lys Ser Cys Arg Val Val Gly Ser Ala Gly Ser Asp
                180                 185                 190 cag aag gtg aag ctg ctg aaa gaa ttt ggt ttt gat gat gcc ttc aat        624
Gln Lys Val Lys Leu Leu Lys Glu Phe Gly Phe Asp Asp Ala Phe Asn
            195                 200                 205 tac aaa tgt gaa aca gac ttg gat gct gca ttg agc agg tac ttc ccc        672
Tyr Lys Cys Glu Thr Asp Leu Asp Ala Ala Leu Ser Arg Tyr Phe Pro
210                 215                 220 aga ggt ata gat atc tac ttt gac aat gtg ggt gga cgc atg tta gaa        720
Arg Gly Ile Asp Ile Tyr Phe Asp Asn Val Gly Gly Arg Met Leu Glu
225                 230                 235                 240 gct gtt ctg aac cac atc aac atg aaa gct cgg att cca ctc tgt ggg        768
Ala Val Leu Asn His Ile Asn Met Lys Ala Arg Ile Pro Leu Cys Gly
                245                 250                 255 atg atc tct cag tat aat cag gag tgg aag caa cgt ttt gga gtg aga        816
Met Ile Ser Gln Tyr Asn Gln Glu Trp Lys Gln Arg Phe Gly Val Arg
                260                 265                 270 aac ctg ctg aac ttg gtg ggg aaa tgt gca aag atg gaa ggc ttc atg        864
Asn Leu Leu Asn Leu Val Gly Lys Cys Ala Lys Met Glu Gly Phe Met
            275                 280                 285 tct ggg caa tac cat cat cgc atg ggg gag ttc ttt gag gag atg aca        912
Ser Gly Gln Tyr His His Arg Met Gly Glu Phe Phe Glu Glu Met Thr
        290                 295                 300 ggg tac atc aag caa gga aaa atc aaa tac aag gaa gat gtt aag gtg        960
Gly Tyr Ile Lys Gln Gly Lys Ile Lys Tyr Lys Glu Asp Val Lys Val
305                 310                 315                 320 ggg ttg gac agt ttc ttg gaa gct ttt aac tcc atg ttt act gga gaa       1008
Gly Leu Asp Ser Phe Leu Glu Ala Phe Asn Ser Met Phe Thr Gly Glu
                325                 330                 335 aat att ggt aaa cct gtc att tat ctg ggg cca ccg cta cca aaa           1053
Asn Ile Gly Lys Pro Val Ile Tyr Leu Gly Pro Pro Leu Pro Lys
                340                 345                 350
```

```
<210> SEQ ID NO 2
<211> LENGTH: 351
<212> TYPE: PRT
<213> ORGANISM: Pinus Taeda

<400> SEQUENCE: 2

Met Glu Gln Arg Val Pro Asn Arg Glu Leu Ile Leu Val Ala Tyr Ala
1               5                   10                  15

Asn Glu Gly Pro Val Thr Asp Ser His Leu Asn Ile Arg Glu Thr Lys
            20                  25                  30

Leu Asp Leu Gly Ser Val Gly Lys Asp Gly Ser Ser Gly Asp Val Ala
        35                  40                  45

Val Gln Asn Leu Trp Ile Ser Val Asp Pro Tyr Leu Arg Gln Leu Met
    50                  55                  60

Lys Glu Ser Asp Asp Gly Leu Tyr Leu Pro Ser Phe Pro Leu Asn Gln
65                  70                  75                  80

Ala Ile Arg Ser Ile Leu Val Gly Lys Val Val Ala Ser Ala Asn Pro
                85                  90                  95

Ala Phe Glu Val Gly Asp Ile Val Ser Gly Phe Tyr Gln Val Ser Glu
            100                 105                 110

Tyr Ala Ile Val Pro Arg Gly Asp Leu Met Lys Ile Asp Thr Ser Val
        115                 120                 125

Val Lys Pro Ser Asp Tyr Leu Gly Leu Leu Gly Met Pro Ala Leu Thr
    130                 135                 140

Ala Trp Ala Gly Phe Ile Ile Val Gly Glu Pro Lys Pro Gly Asp Glu
145                 150                 155                 160

Val Phe Val Ser Ala Ala Gly Ser Val Gly Met Leu Val Gly Gln
                165                 170                 175

Leu Ala Lys Ile Lys Ser Cys Arg Val Val Gly Ser Ala Gly Ser Asp
                180                 185                 190

Gln Lys Val Lys Leu Lys Glu Phe Gly Phe Asp Asp Ala Phe Asn
            195                 200                 205

Tyr Lys Cys Glu Thr Asp Leu Asp Ala Ala Leu Ser Arg Tyr Phe Pro
        210                 215                 220

Arg Gly Ile Asp Ile Tyr Phe Asp Asn Val Gly Gly Arg Met Leu Glu
225                 230                 235                 240

Ala Val Leu Asn His Ile Asn Met Lys Ala Arg Ile Pro Leu Cys Gly
                245                 250                 255

Met Ile Ser Gln Tyr Asn Gln Glu Trp Lys Gln Arg Phe Gly Val Arg
            260                 265                 270

Asn Leu Leu Asn Leu Val Gly Lys Cys Ala Lys Met Glu Gly Phe Met
        275                 280                 285

Ser Gly Gln Tyr His His Arg Met Gly Glu Phe Phe Glu Glu Met Thr
    290                 295                 300

Gly Tyr Ile Lys Gln Gly Lys Ile Lys Tyr Lys Glu Asp Val Lys Val
305                 310                 315                 320

Gly Leu Asp Ser Phe Leu Glu Ala Phe Asn Ser Met Phe Thr Gly Glu
                325                 330                 335

Asn Ile Gly Lys Pro Val Ile Tyr Leu Gly Pro Pro Leu Pro Lys
            340                 345                 350

<210> SEQ ID NO 3
<211> LENGTH: 21
<212> TYPE: PRT
<213> ORGANISM: Pinus Taeda
```

```
<400> SEQUENCE: 3

Glu Leu Ile Leu Val Ala Tyr Ala Asn Glu Gly Pro Val Thr Asp Ser
1               5                   10                  15

His Leu Asn Ile Arg
            20

<210> SEQ ID NO 4
<211> LENGTH: 21
<212> TYPE: PRT
<213> ORGANISM: Pinus Taeda

<400> SEQUENCE: 4

Asp Gly Ser Ser Gly Asp Val Ala Val Gln Asn Leu Trp Ile Ser Val
1               5                   10                  15

Asp Pro Tyr Leu Arg
            20

<210> SEQ ID NO 5
<211> LENGTH: 18
<212> TYPE: PRT
<213> ORGANISM: Pinus Taeda

<400> SEQUENCE: 5

Glu Ser Asp Asp Gly Leu Tyr Leu Pro Ser Phe Pro Leu Asn Gln Ala
1               5                   10                  15

Ile Arg

<210> SEQ ID NO 6
<211> LENGTH: 17
<212> TYPE: DNA
<213> ORGANISM: artificial sequence
<220> FEATURE:
<221> NAME/KEY: misc_feature
<223> OTHER INFORMATION: Description of Artificial Sequence:
      Oligonucleotide Primer

<400> SEQUENCE: 6
ggaatccagc ccatgca                                              17

<210> SEQ ID NO 7
<211> LENGTH: 17
<212> TYPE: DNA
<213> ORGANISM: artificial sequence
<220> FEATURE:
<221> NAME/KEY: misc_feature
<223> OTHER INFORMATION: Description of Artificial Sequence: T3 Forward
      Primer

<400> SEQUENCE: 7
attaaccctc actaaag                                              17

<210> SEQ ID NO 8
<211> LENGTH: 23
<212> TYPE: DNA
<213> ORGANISM: artificial sequence
<220> FEATURE:
<221> NAME/KEY: misc_feature
<223> OTHER INFORMATION: Description of Artificial Sequence: Primer
      APDBR-NT1

<400> SEQUENCE: 8
agtgattgta tgtacaattg agg                                       23
```

-continued

```
<210> SEQ ID NO 9
<211> LENGTH: 17
<212> TYPE: DNA
<213> ORGANISM: artificial sequence
<220> FEATURE:
<221> NAME/KEY: misc_feature
<223> OTHER INFORMATION: Description of Artificial Sequence: T7 Primer

<400> SEQUENCE: 9
aatacgactc actatag                                                      17

<210> SEQ ID NO 10
<211> LENGTH: 30
<212> TYPE: DNA
<213> ORGANISM: artificial sequence
<220> FEATURE:
<221> NAME/KEY: misc_feature
<223> OTHER INFORMATION: Description of Artificial Sequence: 5' Primer 1

<400> SEQUENCE: 10
gatccatgga gcagagagtt ccaaacagag                                        30

<210> SEQ ID NO 11
<211> LENGTH: 26
<212> TYPE: DNA
<213> ORGANISM: artificial sequence
<220> FEATURE:
<221> NAME/KEY: misc_feature
<223> OTHER INFORMATION: Description of Artificial Sequence: 5' Primer 2

<400> SEQUENCE: 11
catggagcag agagttccaa acagag                                            26

<210> SEQ ID NO 12
<211> LENGTH: 25
<212> TYPE: DNA
<213> ORGANISM: artificial sequence
<220> FEATURE:
<221> NAME/KEY: misc_feature
<223> OTHER INFORMATION: Description of Artificial Sequence: 3' Primer 3

<400> SEQUENCE: 12
catccagaat ttattttggt agggg                                             25

<210> SEQ ID NO 13
<211> LENGTH: 29
<212> TYPE: DNA
<213> ORGANISM: artificial sequence
<220> FEATURE:
<221> NAME/KEY: misc_feature
<223> OTHER INFORMATION: Description of Artificial Sequence: 3' Primer 4

<400> SEQUENCE: 13
aattcatcca gaatttattt tggtagggg                                         29
```

ARYL PROPENAL DOUBLE BOND REDUCTASE

CROSS-REFERENCE(S) TO RELATED APPLICATION(S)

This application claims the benefit of U.S. Provisional Patent Application Ser. No. 60/192,266, filed on Mar. 27, 2000, under 35 U.S.C. 119.

GOVERNMENT RIGHTS

This invention was funded in part by the National Science Foundation, Contract No. MCB 9976684. The United States Government has certain rights in the invention.

FIELD OF THE INVENTION

This application relates to aryl propenal double bond reductase proteins, to nucleic acid molecules and vectors encoding aryl propenal double bond reductase proteins, and to methods of altering the composition of plant material, such as wood, by altering the level of expression of one or more aryl propenal double bond reductase proteins within a plant.

BACKGROUND OF THE INVENTION

Lignans are a large, structurally diverse, class of vascular plant metabolites having a wide range of physiological functions and pharmacologically important properties (Ayres, D. C., and Loike, J. D. in *Chemistry and Pharmacology of Natural Products*. Lignans. Chemical, Biological and Clinical Properties, Cambridge University Press, Cambridge, England (1990); Lewis et al., in Chemistry of the Amazon, Biodiversity Natural Products, and Environmental Issues, 588, (P. R. Seidl, O. R. Gottlieb and M. A. C. Kaplan) 135–167, ACS Symposium Series, Washington D.C. (1995)). Because of their pronounced antibiotic properties (Markkanen, T. et al., *Drugs Exptl. Clin. Res.* 7:711–718 (1981)), antioxidant properties (Fauré, M. et al., *Phytochemistry* 29:3773–3775 (1990); Osawa, T. et al., *Agric. Biol. Chem.* 49:3351–3352 (1985)) and antifeedant properties (Harmatha, J., and Nawrot, J., *Biochem. Syst. Ecol.* 12:95–98 (1984)), a major role of lignans in vascular plants is to help confer resistance against various opportunistic biological pathogens and predators. Lignans have also been proposed as cytokinins (Binns, A. N. et al., *Proc. Natl. Acad. Sci. USA* 84:980–984 (1987)) and as intermediates in lignification (Rahman, M. M. A. et al., *Phytochemistry* 29:1861–1866 (1990)), suggesting a critical role in plant growth and development. Lignans can contribute extensively to heartwood formation/generation by enhancing the resulting heartwood color, quality, fragrance and durability.

In addition to their functions in plants, lignans also have important pharmacological roles. For example, podophyllotoxin, as its etoposide and teniposide derivatives, is an example of a plant compound that has been successfully employed as an anticancer agent (Ayres, D. C., and Loike, J. D. in *Chemistry and Pharmacology of Natural Products*. Lignans. Chemical, Biological and Clinical Properties, Cambridge University Press, Cambridge, England (1990)). Antiviral properties have also been reported for selected lignans. For example, (−)-arctigenin (Schröder, H. C. et al., *Z. Naturforsch.* 45c, 1215–1221 (1990)), (−)-trachelogenin (Schröder, H. C. et al., *Z. Naturforsch.* 45c, 1215–1221 (1990)) and nordihydroguaiaretic acid (Gnabre, J. N. et al., *Proc. Natl. Acad. Sci. USA* 92:11239–11243 (1995)) are each effective against HIV due to their pronounced reverse transcriptase inhibitory activities. Some lignans, e.g., matairesinol (Nikaido, T. et al., *Chem. Pharm. Bull.* 29:3586–3592 (1981)), inhibit cAMP-phosphodiesterase, whereas others enhance cardiovascular activity, e.g., syringaresinol β-D-glucoside (Nishibe, S. et al., *Chem. Pharm. Bull.* 38:1763–1765 (1990)). There is also a high correlation between the presence, in the diet, of the "mammalian" lignans or "phytoestrogens", enterolactone and enterodiol, formed following digestion of high fiber diets, and reduced incidence rates of breast and prostate cancers (so-called chemoprevention) (Axelson, M., and Setchell, K. D. R., *FEBS Lett.* 123:337–342 (1981); Adlercreutz et al., *J. Steroid Biochem. Molec. Biol.* 41:3–8 (1992); Adlercreutz et al., *J. Steroid Biochem. Molec. Biol.* 52:97–103 (1995)). The "mammalian lignans," in turn, are considered to be derived from lignans such as matairesinol and secoisolariciresinol (Boriello et al., *J. Applied Bacteriol.*, 58:37–43 (1985)).

The biosynthetic pathways to the lignans are only now being defined. In this regard, loblolly pine (*Pinus taeda*) is a popular and commercially important softwood species in the United States, and has been used as a model for studies on lignin biosynthesis and monolignol regulation. Moreover, its cell suspension cultures accumulate various 8-5' linked lignans, namely dehydrodiconiferyl alcohol (DDC) and dihydrodehydrodiconiferyl alcohol (DDDC), as well as the 8-8' linked lignan, pinoresinol, when placed in a culturing medium containing 8% sucrose and 20 mM KI solution. The present inventors have utilized these cell cultures to characterize enzymes involved in the double bond hydrogenation system of DDC and coniferyl alcohol since the resulting metabolites help determine the color, durability and resistance of the wood, particularly the heartwood.

Thus, in one aspect, the present invention provides a cDNA molecule (SEQ ID NO:1) isolated from loblolly pine (*Pinus taeda*) cells, and the encoded aryl propenal double-bond reductase (SEQ ID NO:2). Aryl propenal double-bond reductase (SEQ ID NO:2) expressed from the isolated cDNA molecule (SEQ ID NO:1) was found to regiospecifically reduce the double-bond of dehydrodiconiferyl aldehyde (DDCAL) to afford dihydrodehydrodiconiferyl aldehyde (DDDCAL) in the presence of [4R]-NADPH. The recombinant aryl propenal double-bond reductase (SEQ ID NO:2) was also capable of reducing coniferyl aldehyde to dihydroconiferyl aldehyde, and *P. taeda* soluble enzyme preparations also catalyzed the reduction of dihydroconiferyl aldehyde to give dihydroconiferyl alcohol, i.e., the aryl propenal double-bond reductase (SEQ ID NO:2) acts on both monomeric and dimeric aryl propenals.

SUMMARY OF THE INVENTION

In one aspect, the present invention provides isolated nucleic acid molecules that each: (a) encode an aryl propenal double bond reductase; and (b) hybridize to a nucleic acid molecule consisting of the complement of the nucleic acid sequence set forth in SEQ ID NO:1 under conditions of 1×SSC at 55° C. for one hour. Some nucleic acid molecules of this aspect of the invention are cDNA molecules. An exemplary nucleic acid molecule of the invention is the cDNA molecule consisting of the nucleic acid sequence set forth in SEQ ID NO:1 that encodes the aryl propenal double bond reductase consisting of the amino acid sequence set forth in SEQ ID NO:2.

In another aspect, the present invention provides isolated nucleic acid molecules that each encode an aryl propenal double bond reductase that is at least 50% identical (such as at least 70% identical, or at least 80% identical, or at least 90% identical) to the aryl propenal double bond reductase consisting of the amino acid sequence set forth in SEQ ID NO:2. The present invention also provides vectors that include a nucleic acid molecule of the invention, and host cells (such as plant cells) that include a vector of the invention. Thus, in one embodiment, the present invention provides vectors that each comprise a nucleic acid molecule that: (a) encodes an aryl propenal double bond reductase; and (b) hybridizes to the complement of SEQ ID NO:1 under conditions of 1×SSC, 55° C. for one hour.

In yet another aspect, the present invention provides isolated aryl propenal double bond reductase proteins that are at least 50% identical (such as at least 70% identical, or at least 80% identical, or at least 90% identical) to the aryl propenal double bond reductase consisting of the amino acid sequence set forth in SEQ ID NO:2.

In a further aspect, the present invention provides methods of enhancing the level of aryl propenal double bond reductase in a plant, the methods each comprising the steps of: (a) introducing into a plant an expression vector comprising a nucleic acid molecule that: (1) encodes an aryl propenal double bond reductase; (2) hybridizes to the complement of SEQ ID NO:1 under conditions of 1×SSC at 55° C. for one hour; and (b) expressing the aryl propenal double bond reductase within the plant.

The present invention also provides methods of inhibiting the expression of aryl propenal double bond reductase in a plant, the methods comprising the steps of: (a) introducing into a plant an expression vector that comprises a nucleic acid molecule that is in antisense orientation relative to a promoter, the nucleic acid molecule hybridizing to the nucleic acid molecule consisting of the nucleic acid sequence set forth in SEQ ID NO:1 under conditions of 1×SSC, 55° C. for one hour; and (b) transcriptionally expressing the nucleic acid molecule in the plant.

The nucleic acid molecules, proteins and methods of the invention are useful for a variety of purposes, including altering the amount and/or type of lignans produced by plant cells. For example, enhancing lignan production by expressing a nucleic acid molecule or protein of the invention in a plant can enhance plant defense against predators (e.g., herbivores) and pathogens (e.g., fungal, bacterial, and viruses), as well as enhance desirable qualities of color, durability and integrity of woody plant tissues (such as heartwood and sapwood). Again by way of example, expression in plants of a nucleic acid molecule of the invention in antisense orientation can inhibit the production of aryl propenal double bond reductase and therefore of one or more plant lignans.

DETAILED DESCRIPTION OF THE PREFERRED EMBODIMENT

Unless specifically defined herein, all terms used herein have the same meaning as they would to one skilled in the art of the present invention. Practitioners are particularly directed to Sambrook et al. (1989) *Molecular Cloning: A Laboratory Manual*, $2^{nd}$ ed., Cold Spring Harbor Press, Plainsview, N.Y. (1989), and Ausubel et al., *Current Protocols in Molecular Biology* (Supplement 47), John Wiley & Sons, New York (1999), for definitions and terms of the art.

The term "isolated" used with respect to a nucleic acid molecule or polypeptide of the invention means a molecule that is substantially free from cellular components that are associated with the nucleic acid molecule or polypeptide as it is found in nature. As used in this context, the term "substantially free from cellular components" means that the nucleic acid molecule or polypeptide is purified to a purity level of greater than 80% (such as greater than 90%, greater than 95%, or greater than 99%). Moreover, the terms "isolated nucleic acid molecule" and "isolated aryl propenal double bond reductase" include nucleic acid molecules and polypeptides which do not naturally occur, and have been produced by synthetic means. An isolated nucleic acid molecule or polypeptide generally resolves as a single, predominant, band by gel electrophoresis, and yields a nucleic acid or amino acid sequence profile consistent with the presence of a predominant nucleic acid molecule or polypeptide.

The term "aryl propenal double bond reductase" refers to an enzyme that catalyzes the reduction of the propenal side chain of one or more phenylpropanoid molecule.

The term "percent identity" or "percent identical" when used in connection with the aryl propenal double bond reductases of the present invention, is defined as the percentage of amino acid residues in a candidate polypeptide sequence that are identical with a subject polypeptide molecule sequence (such as the polypeptide amino acid sequence of SEQ ID NO:2), after aligning the candidate and subject sequences to achieve the maximum percent identity. When making the comparison, no gaps are introduced into the candidate polypeptide sequence in order to achieve the best alignment.

Amino acid sequence identity can be determined in the following manner. The subject polypeptide sequence is used to search a polypeptide sequence database, such as the GenBank database (accessible at web site http://www.ncbi.nln.nih.gov/blast/), using the BLASTP program. The program is used in the ungapped mode. Default filtering is used to remove sequence homologies due to regions of low complexity. The default parameters of BLASTP are utilized. Filtering for sequences of low complexity utilizes the SEG program.

The term "vector" refers to a nucleic acid molecule, usually double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing the insert nucleic acid molecule, and, optionally, translating the transcript into a polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated. The term "vector" includes the T-DNA of a Ti plasmid.

The term "expression vector" refers to a vector that includes the necessary elements that permit transcribing the insert nucleic acid molecule, and, optionally, translating the transcript into a polypeptide.

The term "gymnosperm" refers to a class of plants that produce seeds that are not enclosed in an ovary.

As used herein, the abbreviation "SSC" refers to a buffer used in nucleic acid hybridization solutions. One liter of the 20× (twenty times concentrate) stock SSC buffer solution (pH 7.0) contains 175.3 g sodium chloride and 88.2 g sodium citrate.

Denhardt's reagent is utilized in nucleic acid hybridization solutions. 500 ml of 50× Denhardt's reagent (the 50 fold concentrate) includes 5 g Ficoll (Type 400, Pharmacia), 5 g polyvinylpyrrolidone, 5 g bovine serum albumin (Fraction V, Sigma) and water to 500 ml.

As described in Example 2, the inventors isolated aryl propenal double bond reductase protein from cultured *Pinus taeda* cells. The purified protein was cleaved with trypsin to yield three peptide sequences ELILVAYANEGPVTD-SHLNIR (SEQ ID NO:3), DGSSGDVAVQNLWISVD-PYLR (SEQ ID NO:4), and ESDDGLYLPSFPLNQAIR (SEQ ID NO:5) which were used to screen the GenBank database. An expressed sequence tag (EST) (GenBank accession No. AA556927) was identified that encoded all three peptides (SEQ ID NOS:3, 4, 5).

As set forth in Example 3 herein, PCR amplification was utilized to obtain a longer cDNA that corresponded to the partial-length cDNA set forth in GenBank accession No. AA556927 and that encoded a complete aryl propenal double bond reductase protein. The resulting cDNA molecule is set forth in SEQ ID NO:1, and encodes the aryl propenal double bond reductase protein having the amino acid sequence set forth in SEQ ID NO:2. As set forth in Example 3, the aryl propenal double bond reductase cDNA (SEQ ID NO:1) was expressed in *E. coli* and shown to be enzymatically active.

Thus, in one aspect, the present invention provides isolated nucleic acid molecules that each: (a) encode an aryl propenal double bond reductase; and (b) hybridize to a nucleic acid molecule consisting of the complement of the nucleic acid sequence set forth in SEQ ID NO:1 under conditions of 1×SSC at 55° C. for one hour. Hybridization can be conducted, for example, by utilizing the technique of hybridizing radiolabelled nucleic acid probes to nucleic acids immobilized on nitrocellulose filters or nylon membranes as set forth at pages 9.52 to 9.55 of Molecular Cloning, A Laboratory Manual (2nd edition), J. Sambrook, E. F. Fritsch and T. Maniatis eds, the cited pages of which are incorporated herein by reference. An exemplary hybridization protocol is set forth in Example 4 herein. Some nucleic acid molecules of this aspect of the invention hybridize to the complement of the nucleic acid sequence set forth in SEQ ID NO:1 under conditions of 1×SSC at 65° C.

The present invention also provides isolated nucleic acid molecules that each encode an aryl propenal double bond reductase that is at least 50% identical (such as at least 70% identical, or at least 80% identical, or at least 90% identical) to the aryl propenal double bond reductase consisting of the amino acid sequence set forth in SEQ ID NO:2.

The nucleic acid molecules of the invention that encode an aryl propenal double bond reductase can be isolated by using a variety of cloning techniques known to those of ordinary skill in the art: For example, all, or portions of, the cDNA molecule having the sequence set forth in SEQ ID NO:1 can be used as a hybridization probe to screen a plant genomic or cDNA library. The technique of hybridizing radiolabelled nucleic acid probes to nucleic acids immobilized on nitrocellulose filters or nylon membranes can be used to screen the genomic or cDNA library. Exemplary hybridization and wash conditions are: hybridization for 20 hours at 65° C. in 5.0×SSC, 0.5% sodium dodecyl sulfate, 1× Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C.

Again, by way of example, nucleic acid molecules of the invention that encode an aryl propenal double bond reductase can be isolated by the polymerase chain reaction (PCR) described in *The Polymerase Chain Reaction* (K. B. Mullis et al., eds. 1994), incorporated herein by reference. Gobinda et al. (*PCR Methods Applic.* 2:318–22 (1993)), incorporated herein by reference, disclose "restriction-site PCR" as a direct method which uses universal primers to retrieve unknown sequence adjacent to a known locus. First, genomic DNA is amplified in the presence of a linker-primer, that is homologous to a linker sequence ligated to the ends of the genomic DNA fragments, and in the presence of a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Further, by way of example, inverse PCR permits acquisition of unknown sequences starting with primers based on a known region (Triglia, T. et al., *Nucleic Acids Res* 16:8186 (1988), incorporated herein by reference). The method uses several restriction enzymes to generate a suitable fragment in the known region of a gene. The fragment is then circularized by intramolecular ligation and used as a PCR template. Divergent primers are designed from the known region.

Typically, the nucleic acid sequence of a primer useful to amplify nucleic acid molecules of the invention by PCR is based on a conserved region of amino acid sequence of the aryl propenal double bond reductase polypeptides of the invention (such as the aryl propenal double bond reductase polypeptide having the amino acid sequence set forth in SEQ ID NO:2).

In another aspect, the present invention provides vectors that comprise a nucleic acid molecule of the invention. Vectors of the invention include the elements necessary for replication in a target host cell, such as a prokaryotic cell, or a eukaryotic cell. Vectors that are functional in plants are preferably binary plasmids derived from Agrobacterium plasmids. Such vectors are capable of transforming plant cells. Briefly, these vectors typically contain left and right border sequences that are required for integration into the host (plant) chromosome. Typically, between these border sequences is the nucleic acid molecule (such as a cDNA) to be expressed under control of a promoter. In some embodiments, a selectable marker and a reporter gene are also included. The vector also may contain a bacterial origin of replication.

In another aspect, the present invention provides host cells comprising a vector of the invention. Host cells can be prokaryotic or eukaryotic, such as plant cells. For example, one or more vectors of the invention can be introduced into yeast host cells using the polyethylene glycol method, as described by Hinnen (*Proc. Natl. Acad. Sci. USA,* 75:1929 [1978]). Additional yeast transformation protocols are set forth in Gietz et al., *N.A.R.,* 20(17):1425(1992); Reeves et al., *FEMS,* 99(2–3):193–197, (1992), both of which publications are incorporated herein by reference.

The vectors of the invention can be introduced into plant cells using techniques well known to those skilled in the art. These methods include, but are not limited to, (1) direct DNA uptake, such as particle bombardment or electroporation (see, Klein et al., *Nature* 327:70–73 (1987); U.S. Pat. No. 4,945,050), and (2) Agrobacterium-mediated transformation (see, e.g., U.S. Pat. Nos. 6,051,757; 5,731,179; 4,693,976; 4,940,838; 5,464,763; and 5,149,645). Within the cell, the transgenic sequences may be incorporated within the chromosome. The skilled artisan will recognize that different independent insertion events may result in different levels and patterns of gene expression (Jones et al., *EMBO J.* 4:2411–2418 (1985); De Almeida et al., *MGG* 218:78–86 (1989)), and thus that multiple events may have to be screened in order to obtain lines displaying the desired expression level and pattern.

Transgenic plants can be obtained, for example, by transferring vectors that include a selectable marker gene, e.g., the kan gene encoding resistance to kanamycin, into *Agrobacterium tumifaciens* containing a helper Ti plasmid as described in Hoeckema et al., *Nature*, 303:179–181 (1983) and culturing the Agrobacterium cells with leaf slices, or other tissues or cells, of the plant to be transformed as described by An et al., *Plant Physiology*, 81:301–305 (1986). Transformation of cultured plant host cells is normally accomplished through *Agrobacterium tumifaciens*.

Transformed plant calli may be selected through the selectable marker by growing the cells on a medium containing, for example, kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

In addition to the methods described above, several methods are known in the art for transferring cloned DNA and vectors into a wide variety of plant species, including gymnosperms, angiosperms, monocots and dicots (see, e.g., Glick and Thompson, eds., *Methods in Plant Molecular Biology*, CRC Press, Boca Raton, Fla. (1993), incorporated by reference herein). Representative examples include electroporation-facilitated DNA uptake by protoplasts in which an electrical pulse transiently permeabilizes cell membranes, permitting the uptake of a variety of biological molecules, including recombinant DNA (see, e.g., Rhodes et al., *Science*, 240:204–207 (1988)); treatment of protoplasts with polyethylene glycol (see, e.g., Lyznik et al., *Plant Molecular Biology*, 13:151–161 (1989)); and bombardment of cells with DNA-laden microprojectiles which are propelled by explosive force or compressed gas to penetrate the cell wall (see, e.g., Klein et al., *Plant Physiol.* 91:440–444 (1989) and Boynton et al., *Science*, 240(4858):1534–1538 (1988)). A method that has been applied to Rye plants (*Secale cereale*) is to directly inject plasmid DNA, including a selectable marker gene, into developing floral tillers (de la Pena et al., *Nature* 325:274–276 (1987)). Further, plant viruses can be used as vectors to transfer genes to plant cells. Examples of plant viruses that can be used as vectors to transform plants include the Cauliflower Mosaic Virus (see, e.g., Brisson et al., *Nature* 310:511–514 (1984); Other useful techniques include: site-specific recombination using the Cre-lox system (see, U.S. Pat. No. 5,635,381); and insertion into a target sequence by homologous recombination (see, U.S. Pat. No. 5,501,967). Additionally, plant transformation strategies and techniques are reviewed in Birch, R. G., *Ann Rev Plant Phys Plant Mol Biol.*, 48:297 (1997); Forester et al., *Exp. Agric.*, 33:15–33 (1997).

Positive selection markers may also be utilized to identify plant cells that include a vector of the invention. For example, U.S. Pat. Nos. 5,994,629, 5,767,378, and 5,599,670, describe the use of a beta-glucuronidase transgene and application of cytokinin-glucuronide for selection, and use of mannophosphatase or phosphmanno-isomerase transgene and application of mannose for selection.

The cells which have been transformed may be grown into plants by a variety of art-recognized means. See, for example, McConnick et al., *Plant Cell Reports* 5:81–84 (1986). These plants may then be grown, and either selfed or crossed with a different plant strain, and the resulting homozygotes or hybrids having the desired phenotypic characteristic identified. Two or more generations may be grown to ensure that the subject phenotypic characteristic is stably maintained and inherited and then seeds harvested to ensure the desired phenotype or other property has been achieved.

The following are representative plant species that are suitable for genetic manipulation in accordance with the present invention. The citations are to representative publications disclosing genetic transformation protocols that can be used to genetically transform the listed plant species. Rice (Alam, M. F. et al., *Plant Cell Rep.* 18:572–575 (1999)); maize (U.S. Pat. Nos. 5,177,010 and 5,981,840); wheat (Ortiz, J. P. A., et al., *Plant Cell Rep.* 15:877–881 (1996)); tomato (U.S. Pat. No. 5,159,135); potato (Kumar, A., et al., *Plant J.* 9:821–829 (1996)); cassava (Li, H. -Q., et al., *Nat. Biotechnology* 14:736–740 (1996)); lettuce (Michelmore, R., et al., *Plant Cell Rep.* 6:439–442 (1987)); tobacco (Horsch, R. B., et al., *Science* 227:1229–1231 (1985)); cotton (U.S. Pat. Nos. 5,846,797 and 5,004,863); grasses (U.S. Pat. Nos. 5,187,073 and 6,020,539); peppermint (X. Niu et al., *Plant Cell Rep.* 17:165–171 (1998)); citrus plants (Pena, L. et al., *Plant Sci.* 104:183–191 (1995)); caraway (F. A. Krens, et al., *Plant Cell Rep.*, 17:39–43 (1997)); banana (U.S. Pat. No. 5,792,935); soybean (U.S. Pat. Nos. 5,416, 011; 5,569,834; 5,824,877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); brassica (U.S. Pat. Nos. 5,188,958; 5,463, 174 and 5,750,871); and cereals (U.S. Pat. No. 6,074,877).

Cultures of mammalian host cells and other host cells that do not have rigid cell membrane barriers are usually transformed using the calcium phosphate method as originally described by Graham and Van der Eb (*Virology*, 52:546 [1978]) and modified as described in sections 16.32–16.37 of Sambrook et al., supra. However, other methods for introducing DNA into cells such as Polybrene (Kawai and Nishizawa, *Mol. Cell. Biol.*, 4:1172 [1984]), protoplast fusion (Schaffner, *Proc. Natl. Acad. Sci. USA*, 77:2163 [1980]), electroporation (Neumann et al., *EMBO J.*, 1:841 [1982]), and direct microinjection into nuclei (Capecchi, *Cell*, 22:479 [1980]) may also be used. Additionally, animal transformation strategies are reviewed in Monastersky G. M. and Robl, J. M., *Strategies in Transgenic Animal Science*, ASM Press, Washington, D.C., 1995, incorporated herein by reference.

Prokaryotic host cells are preferably transformed using the calcium chloride method as described in section 1.82 of Sambrook et al., supra. Alternatively, electroporation may be used for transformation of these cells. Prokaryote transformation techniques are set forth in Dower, W. J., in Genetic Engineering, Principles and Methods, 12:275–296, Plenum Publishing Corp., 1990; Hanahan et al., *Meth. Enzymol.*, 204:63 (1991).

In another aspect, the present invention provides isolated aryl propenal double bond reductase proteins that are at least 50% identical (such as at least 70% identical, or at least 80% identical, or at least 90% identical) to the aryl propenal double bond reductase consisting of the amino acid sequence set forth in SEQ ID NO:2.

Aryl propenal double bond reductases of the invention can be prepared, for example, by expressing a nucleic acid molecule encoding an aryl propenal double bond reductase in a suitable host cell, such as *E. coli*. By way of representative example, a nucleic acid molecule (such as a cDNA molecule) encoding an aryl propenal double bond reductases is cloned into a plasmid vector, such as a Bluescript plasmid (available from Stratagene, Inc., La Jolla, Calif.). The recombinant vector is then introduced into an *E. coli* strain (such as *E. coli* XL1-Blue, also available from Stratagene, Inc.) and the aryl propenal double bond reductase is expressed in *E. coli* and then purified. For example, *E. coli* XL 1-Blue harboring a Bluescript vector including a cDNA molecule encoding an aryl propenal double bond reductase is grown overnight at 37° C. in LB medium containing 100 µg ampicillin/ml. A 50 µl aliquot of the overnight culture is used to inoculate 5 ml of fresh LB medium containing ampicillin, and the culture grown at 37° C. with vigorous agitation to $A_{600}$=0.5 before induction with 1 mM IPTG. After an additional two hours of growth, the suspension is centrifuged (1000× g, 15 min, 4° C.), the media removed, and the pelleted cells resuspended in 1 ml of cold buffer that preferably contains 1 mM EDTA and one or more proteinase inhibitors. The cells can be disrupted by sonication with a microprobe. The chilled sonicate is cleared by centrifugation and the expressed, recombinant, aryl propenal double bond reductase purified from the supernatant by art-recognized protein purification techniques, such as those described herein.

Again by way of example, aryl propenal double bond reductases of the invention can be prepared by expressing a nucleic acid molecule encoding an aryl propenal double bond reductase in insect cells using the recombinant baculovirus, *Autographa californica* nuclear polyhedrosis virus (AcNPV; M. D. Summers and G. E. Smith, *A Manual of Methods for Baculovirus Vectors and Insect Cell Culture Procedures* [1986]; Luckow et al., *Bio-technology*, 6:47–55 [1987]). Infection of insect cells (such as cells of the species *Spodoptera frugiperda*) with the recombinant baculoviruses allows for the production of large amounts of aryl propenal double bond reductase proteins. In addition, the baculovirus system has other important advantages for the production of recombinant aryl propenal double bond reductase proteins. For example, baculoviruses do not infect humans and can therefore be safely handled in large quantities. In the baculovirus system, a DNA construct is prepared including a DNA segment encoding aryl propenal double bond reductase and a vector. The vector may comprise the polyhedron gene promoter region of a baculovirus, the baculovirus flanking sequences necessary for proper cross-over during recombination (the flanking sequences comprise about 200–300 base pairs adjacent to the promoter sequence) and a bacterial origin of replication which permits the construct to replicate in bacteria. The vector is constructed so that (i) the DNA segment is placed adjacent (or operably linked or "downstream" or "under the control of") to the polyhedron gene promoter and (ii) the promoter/aryl propenal double bond reductase combination is flanked on both sides by 200–300 base pairs of baculovirus DNA (the flanking sequences).

To produce the aryl propenal double bond reductase DNA construct, a cDNA clone encoding the full length aryl propenal double bond reductase is obtained using methods such as those described herein. The DNA construct is contacted in a host cell with baculovirus DNA of an appropriate baculovirus (that is, of the same species of baculovirus as the promoter encoded in the construct) under conditions such that recombination is effected. The resulting recombinant baculoviruses encode the full aryl propenal double bond reductase. For example, an insect host cell can be cotransfected or transfected separately with the DNA construct and a functional baculovirus. Resulting recombinant baculoviruses can then be isolated and used to infect cells to effect production of the aryl propenal double bond reductase. Host insect cells include, for example, *Spodoptera frugiperda* cells, that are capable of producing a baculovirus-expressed aryl propenal double bond reductase. Insect host cells infected with a recombinant baculovirus of the present invention are then cultured under conditions allowing expression of the baculovirus-encoded aryl propenal double bond reductase.

Again by way of example, aryl propenal double bond reductases of the invention can be prepared by expressing a nucleic acid molecule encoding an aryl propenal double bond reductase in yeasts. The baker's yeast *Saccharomyces cerevisiae*, is a commonly used yeast, although several other strains are available. The plasmid YRp7 (Stinchcomb et al., *Nature*, 282:39 [1979]; Kingsman et al., *Gene* 7:141 [1979]; Tschemper et al., *Gene*, 10:157 [1980]) is commonly used as an expression vector in Saccharomyces. This plasmid contains the trp1 gene that provides a selection marker for a mutant strain of yeast lacking the ability to grow in tryptophan, such as strains ATCC No. 44,076 and PEP4-1 (Jones, *Genetics*, 85:12 [1977]). The presence of the trp1 lesion as a characteristic of the yeast host cell genome then provides an effective environment for detecting transformation by growth in the absence of tryptophan. Yeast host cells are generally transformed using the polyethylene glycol method, as described by Hinnen (*Proc. Natl. Acad. Sci. USA*, 75:1929 [1978]). Additional yeast transformation protocols are set forth in Gietz et al., *N.A.R.*, 20(17):1425(1992); Reeves et al., *FEMS*, 99(2–3):193–197, (1992), both of which publications are incorporated herein by reference.

Suitable promoting sequences in yeast vectors include the promoters for 3-phosphoglycerate kinase (Hitzeman et al.,*J. Biol. Chem.*, 255:2073 [1980]) or other glycolytic enzymes (Hess et al., *J. Adv. Enzyme Reg.* 7:149 [1968]; Holland et al., *Biochemistry*, 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Prokaryotes may also be used as host cells for expression of aryl propenal double bond reductases of the invention. Suitable prokaryotic host cells include *E. coli* K12 strain 94 (ATCC No. 31,446), *E. coli* strain W3110 (ATCC No. 27,325) *E. coli* X1776 (ATCC No. 31,537), and *E. coli* B; however many other strains of *E. coli*, such as HB101, JM101, NM522, NM538, NM539, and many other species and genera of prokaryotes including bacilli such as *Bacillus subtilis*, other enterobacteriaceae such as *Salmonella typhimurium* or *Serratia marcesans*, and various Pseudomonas species may all be used as hosts. Prokaryotic host cells or other host cells with rigid cell walls are preferably transformed using the calcium chloride method as described in section 1.82 of Sambrook et al., supra. Alternatively, electroporation may be used for transformation of these cells. Prokaryote transformation techniques are set forth in Dower, W. J., in Genetic Engineering, Principles and Methods, 12:275–296, Plenum Publishing Corp., 1990; Hanahan et al., *Meth. Enzymol.*, 204:63 (1991).

Plants may also be used as host cells for expression of aryl propenal double bond reductases of the invention. Typically, a vector including a nucleic acid molecule encoding an aryl propenal double bond reductase is introduced into a plant cell by any art-recognized means, such as are set forth herein. One or more plants are regenerated from the cells and propagated. The aryl propenal double bond reductase is expressed within the plants (or within plant cell cultures containing the vector) and can be purified therefrom. In some embodiments, the nucleic acid molecule encoding an aryl propenal double bond reductase is under the control of an inducible promoter within the vector. Thus, the nucleic acid molecule will not be transcribed except in response to the specific stimulus.

Representative examples of art-recognized techniques for purifying, or partially purifying, aryl propenal double bond reductase from biological material, such as from prokaryotic cells or eukaryotic cells that express aryl propenal double bond reductase, are: exclusion chromatography, ion-exchange chromatography, hydrophobic interaction chromatography, reversed-phase chromatography and immobilized metal affinity chromatography.

Hydrophobic interaction chromatography and reversed-phase chromatography are two separation methods based on the interactions between the hydrophobic moieties of a sample and an insoluble, immobilized hydrophobic group present on the chromatography matrix. In hydrophobic interaction chromatography the matrix is hydrophilic and is substituted with short-chain phenyl or octyl nonpolar groups. The mobile phase is usually an aqueous salt solution. In reversed phase chromatography the matrix is silica that has been substituted with longer n-alkyl chains, usually $C_8$ (octylsilyl) or $C_{18}$ (octadecylsilyl). The matrix is less polar than the mobile phase. The mobile phase is usually a mixture of water and a less polar organic modifier.

Separations on hydrophobic interaction chromatography matrices are usually done in aqueous salt solutions, which generally are nondenaturing conditions. Samples are loaded onto the matrix in a high-salt buffer and elution is by a descending salt gradient. Separations on reversed-phase media are usually done in mixtures of aqueous and organic solvents, which are often denaturing conditions. In the case of polypeptide and/or peptide purification, hydrophobic interaction chromatography depends on surface hydrophobic groups and is carried out under conditions which maintain the integrity of the polypeptide molecule. Reversed-phase chromatography depends on the native hydrophobicity of the polypeptide and is carried out under conditions which expose nearly all hydrophobic groups to the matrix, i.e., denaturing conditions.

Ion-exchange chromatography is designed specifically for the separation of ionic or ionizable compounds. The stationary phase (column matrix material) carries ionizable functional groups, fixed by chemical bonding to the stationary phase. These fixed charges carry a counterion of opposite sign. This counterion is not fixed and can be displaced. Ion-exchange chromatography is named on the basis of the sign of the displaceable charges. Thus, in anion ion-exchange chromatography the fixed charges are positive and in cation ion-exchange chromatography the fixed charges are negative.

Retention of a molecule on an ion-exchange chromatography column involves an electrostatic interaction between the fixed charges and those of the molecule, binding involves replacement of the nonfixed ions by the molecule. Elution, in turn, involves displacement of the molecule from the fixed charges by a new counterion with a greater affinity for the fixed charges than the molecule, and which then becomes the new, nonfixed ion.

The ability of counterions (salts) to displace molecules bound to fixed charges is a function of the difference in affinities between the fixed charges and the nonfixed charges of both the molecule and the salt. Affinities in turn are affected by several variables, including the magnitude of the net charge of the molecule and the concentration and type of salt used for displacement.

Solid-phase packings used in ion-exchange chromatography include cellulose, dextrans, agarose, and polystyrene. The exchange groups used include DEAE (diethylaminoethyl), a weak base, that will have a net positive charge when ionized and will therefore bind and exchange anions; and CM (carboxymethyl), a weak acid, with a negative charge when ionized that will bind and exchange cations. Another form of weak anion exchanger contains the PEI (polyethyleneimine) functional group. This material, most usually found on thin layer sheets, is useful for binding polypeptides at pH values above their pI. The polystyrene matrix can be obtained with quaternary ammonium functional groups for strong base anion exchange or with sulfonic acid functional groups for strong acid cation exchange. Intermediate and weak ion-exchange materials are also available. Ion-exchange chromatography need not be performed using a column, and can be performed as batch ion-exchange chromatography with the slurry of the stationary phase in a vessel such as a beaker.

Gel filtration is performed using porous beads as the chromatographic support. A column constructed from such beads will have two measurable liquid volumes, the external volume, consisting of the liquid between the beads, and the internal volume, consisting of the liquid within the pores of the beads. Large molecules will equilibrate only with the external volume while small molecules will equilibrate with both the external and internal volumes. A mixture of molecules (such as proteins) is applied in a discrete volume or zone at the top of a gel filtration column and allowed to percolate through the column. The large molecules are excluded from the internal volume and therefore emerge first from the column while the smaller molecules, which can access the internal volume, emerge later. The volume of a conventional matrix used for protein purification is typically 30 to 100 times the volume of the sample to be fractionated. The absorbance of the column effluent can be continuously monitored at a desired wavelength using a flow monitor.

A technique that is often applied to the purification of polypeptides is High Performance Liquid Chromatography (HPLC). HPLC is an advancement in both the operational theory and fabrication of traditional chromatographic systems. HPLC systems for the separation of biological macromolecules vary from the traditional column chromatographic systems in three ways; (1) the column packing materials are of much greater mechanical strength, (2) the particle size of the column packing materials has been decreased 5- to 10-fold to enhance adsorption-desorption kinetics and diminish bandspreading, and (3) the columns are operated at 10–60 times higher mobile-phase velocity. Thus, by way of non-limiting example, HPLC can utilize exclusion chromatography, ion-exchange chromatography, hydrophobic interaction chromatography, reversed-phase chromatography and immobilized metal affinity chromatography. Art-recognized techniques for the purification of proteins and peptides are set forth in *Methods in Enzymology*, Vol. 182, *Guide to Protein Purification*, Murray P. Deutscher, ed. (1990).

In yet another aspect, the present invention provides methods of enhancing the level of aryl propenal double bond reductase in a plant cell, the methods comprising the steps of: (a) introducing into a plant an expression vector comprising a nucleic acid molecule that: (1) encodes an aryl propenal double bond reductase; (2) hybridizes to the complement of SEQ ID NO:1 under conditions of 1×SSC, 55° C. for one hour; and (b) expressing the aryl propenal double bond reductase within the plant. In some embodiment of the methods of this aspect of the invention the nucleic acid molecule hybridizes to the complement of SEQ ID NO:1 under conditions of 1×SSC at 65° C. for one hour.

In a further aspect, the present invention provides methods for inhibiting the expression of aryl propenal double bond reductase in a plant, the methods comprising the steps of: (a) introducing into a plant an expression vector that comprises a nucleic acid molecule that is in antisense orientation relative to a promoter, the nucleic acid molecule hybridizing to the nucleic acid molecule consisting of the nucleic acid sequence set forth in SEQ ID NO:1 under hybridization conditions of 1×SSC, 55° C. for one hour; and (b) transcriptionally expressing the nucleic acid molecule in the plant. In some embodiments of the methods of this aspect of the invention, the nucleic acid molecule hydribizes to the nucleic acid molecule of SEQ ID NO:1 under conditions of 1×SSC at 65° C. for one hour.

The successful implementation of antisense RNA in plants to inhibit the expression of specific genes has previously been demonstrated (Van der Krol et al., 1990 *Plant Mol. Biol.* 14:457; Visser et al., 1991, *Mol. Gen. Genet.* 225:289; Hamilton et al., 1990, *Nature* 346:284; Stockhaus et al., 1990, *EMBO J.* 9:3013; Hudson et al., 1992, *Plant Physiol.* 98:294; U.S. Pat. Nos. 4,801,340, 5,773,692, 5,723, 761, and 5,959,180). For example, polygalacturonase is responsible for fruit softening during the latter stages of ripening in tomato (Hiatt et al., 1989 in *Genetic Engineering*, Setlow, ed. p. 49; Sheehy et al., 1988, *Proc. Natl. Acad. Sci. USA* 85:8805; Smith et al., 1988, *Nature* 334:724). The integration of antisense constructs into the genome, under the control of the CaMV 35S promoter, has inhibited this softening. Examination of the polygalacturonase mRNA levels showed a 90% suppression of gene expression.

An antisense gene is a DNA sequence produced when a sense gene is inverted relative to its normal presentation for transcription. The "sense" gene refers to the gene which is being targeted for control using the antisense technology, in its normal orientation. An antisense gene may be constructed in a number of different ways provided that it is capable of interfering with the expression of a sense gene. Preferably, the antisense gene is constructed by inverting the coding region of the sense gene relative to its normal presentation for transcription to allow the transcription of its complement, hence the RNAs encoded by the antisense and sense gene are complementary. It is understood that a portion of the antisense gene incorporated into an antisense construct, of the present invention, may be sufficient to effectively interfere with the expression of a sense gene and thus the term "antisense gene" used herein encompasses any functional portion of the full length antisense gene. By the term "functional" it is meant to include a portion of the antisense gene which is effective in interfering with the expression of the sense gene.

The antisense gene need not be perfectly identical to the target gene to inhibit expression. Generally, higher homology can be used to compensate for the use of a shorter antisense gene sequence. Furthermore, the introduced antisense gene sequence need not have the same intron or exon pattern as the target gene, and homology of non-coding segments may be equally effective. Normally, a sequence of between about 25 or 40 nucleotides and about the full length of the target gene sequence should be used, though a sequence of at least about 100 nucleotides is preferred, a sequence of at least about 200 nucleotides is more preferred, and a sequence of at least about 500 nucleotides is especially preferred. The construct is then transformed into plants and the antisense strand of RNA is produced.

Representative plant expression vectors are set forth in F. Guerineau and P. Mullineaux, *Plant Transformation and Expression Vectors*, in Plant Molecular Biology LABFax, eds B. D. Hames and D. Rickwood, ps. 121–147, BIOS Scientific Publishers Limited (1993). Representative methods for introducing an expression vector into a plant are set forth supra, and include Agrobacterium-mediated plant transformation.

Any plant species can be treated in accordance with the methods of the invention, in particular gymnosperm plant species, such as plants of the genus Picea. Representative transformation protocols for Picea species are set forth in D. H. Clapham et al., Molecular Biology of Woody Plants (S. M. Jain and S. C. Minocha, eds) Vol. 2, 105–118 (2000), Kluwer Academic Publishers.

All literature citations herein are incorporated by reference.

EXAMPLE 1

This example describes the materials and methods used in the protein purification and cDNA cloning procedures described in Examples 2 and 3.

Plant Materials—*P. taeda* cell suspension cultures were maintained as described previously (Nose, M., et al., *Phytochemistry* 39, 71–79 (1995)), in medium containing 11 μM 2,4-dichlorophenoxyacetic acid (2,4-D). Cells were harvested by filtration seven days after transfer to fresh media, frozen in liquid nitrogen and stored at −80° C.

General Methods—All molecular biological techniques, unless expressly described below were performed according to standard methods (Sambrook, J., Fritsch, E. F. and Maniatis, T. *Molecular Cloning: A Laboratory Manual*, 3 *volumes, 3rd Ed.* (Cold Spring Harbor Laboratory, Cold Spring Harbor, N.Y., 1994); Ausubel, F. M., et al. *Current Protocols in Molecular Biology*, 2 *volumes* (Greene Publishing Associates and Wiley-Interscience, John Wiley and Sons, NY, 1991)).

Materials—All solvents and chemicals used were reagent or HPLC grade. Coniferyl aldehyde was purchased from Aldrich. Phenyl-Sepharose CL-4B, Mono Q HR5/5 were purchased from Amersham Pharmacia Biotech and adenosine 2',5'-diphosphate-agarose was from Sigma. Taq thermostable DNA polymerase was obtained from Gibco BRL Life Technologies. Competent Top 10 cells and TOPO TA cloning® kit were purchased from Invitrogen, and competent Epicurian Coli® BL21-CodonPlus™ (DE3)-RIL cells were from STRATAGENE. Restriction endonucleases BamHI and EcoRI, and Deep Vent Taq DNA polymerase were obtained from New England Biolabs. The pGEX-4T-1 plasmid and thrombin protease were obtained from Amersham Pharmacia Biotech.

Oligonucleotide primers for polymerase chain reaction (PCR) and sequencing were synthesized by Gibco BRL Life Technologies. Spectra/Por® Membranes (MWCO:3,500) were purchased from Spectrum Laboratories, Inc. and used for gel purification of PCR fragments. MICROCON® YM-100 (MILLIPORE) was used to concentrate gel purified DNA solutions, and DNA concentrations were determined by comparison to a low DNA mass ladder (Gibco BRL) in 1% agarose gels.

Chemical syntheses—(±)-Dehydrodiconiferyl and (±)-dihydrodehydrodiconiferyl alcohols were synthesized as previously described in (Gang, D. R., et al., J. Biol. Chem. 274, 7516–7527 (1999)). [4S-$^3$H] and [4R-$^3$H]NADPH were enzymatically synthesized as described in (Dinkova-Kostova, A. T., et al., J. Biol. Chem. 271, 29473–29482 (1996)).

Dihydroconiferyl aldehyde (DCAL) was synthesized as follows: To a solution of coniferyl alcohol (720 mg, 4 mmol) in methanol (10 ml) was added palladium-charcoal (10%, 100 mg), with the resulting solution stirred under an $H_2$ atmosphere for 4 hours (h) at ambient temperature. After the catalyst was removed by filtration, the resulting solution was evaporated to dryness in vacuo. The resulting residue was dissolved in acetone, subjected to preparative TLC and extracted with acetone; evaporation of the solvent afforded dihydroconiferyl alcohol (DCA, 650 mg, 90%). To the purified DCA (600 mg, 3.3 mmol) in $CH_2Cl_2$ (5 ml) was added DMSO (3.4 ml, 36.6 mmol), triethylamine (1 ml, 13.2 mmol), and pyridine sulfur trioxide (1.58 mg, 9.9 mmol), with the resulting mixture stirred for 30 min at ambient temperature. After reaction, the solution was poured into $H_2O$ in a separatory funnel, extracted with ether, washed successively with saturated ($NH_4$)Cl, saturated $NaHCO_3$, $H_2O$ and saturated NaCl, and finally with $NaSO_4$. The solvent was evaporated and the resulting extract subjected to preparative TLC, with dihydroconiferyl aldehyde extracted with acetone. Evaporation of the solvent afforded dihydroconiferyl aldehyde (202 mg, 1.1 mmol, 33%).

Instrumentation—A Lamda 6 UV/VIS spectrophotometer (Perkin-Elmer) was used for recording all DNA determinations at $OD_{260}$. A Temptronic II thermocycler (Thermolyne) was used for all PCR amplifications. The Wizard Plus SV Minipreps DNA Purification System (Promega) was used to purify plasmid DNA for sequencing using an Applied Biosystems model 373A automated sequencer. All HPLC separations were performed on Millenium™ (Waters Inc.) instrument using either $C_8$ reversed-phase (Waters, Symmetry Shield, 150×3.9 mm internal diameter (i.d.)) or chiral (Advanced Separation Technologies, Inc., Chirobiotic V, 250×4.6 mm i.d.) columns with detection at 280 nm. Amino-terminal protein sequencing was carried out as described previously (Dinkova-Kostova, A. T., et al., J. Biol. Chem. 271, 29473–29482 (1996)). Matrix-assisted laser desorption ionization-time of flight mass spectrometry was performed on a VG 7070 at the Laboratory for Bioanalysis and Biotechnology at Washington State University.

EXAMPLE 2

This example describes the purification of an aryl propenal double bond reductase from a culture of *Pinus taeda* cells.

Crude protein preparation—*P. taeda* cells were transferred to a sterile solution of 8% sucrose, 20 mM KI. After 24 hours (h) incubation under the conditions described in Example 1, the cells were harvested, frozen (liquid $N_2$) and ground in a mortar with a pestle. The resulting powder was homogenized with PVPP (5% w/w) and Tris-HCl buffer (50 mM, pH 7.5) containing dithiothreitol (DTT, 5 mM). The homogenate was centrifuged (10,000 g, 20 min) and the resulting supernatant fractionated with $(NH_4)_2SO_4$. Proteins precipitating between 20 and 60% saturation were recovered by centrifugation (10,000 g, 30 min) with the pellet reconstituted in a minimum amount of Tris-HCl buffer (50 mM, pH 7.5) containing DTT (5 mM) (buffer A).

Hydrophobic (Phenyl Sepharose) chromatography—The crude enzyme preparation was next applied to a Phenyl-Sepharose column (15×1.6 cm) equilibrated in buffer A containing 1 M $(NH_4)_2SO_4$. The column was washed with 60 ml of buffer A and the aryl propenal double bond reductase was eluted using a linear gradient of decreasing concentration of $(NH_4)_2SO_4$ (from 1 M to 0 M in 260 ml). Fractions with aryl propenal double bond reductase activity were frozen until needed.

Affinity (adenosine 2',5'diphosphate agarose) chromatography—The active fractions were next combined, pooled, concentrated and then applied to an affinity adenosine 2',5'diphosphate agarose column (1.0×9.5 cm) previously equilibrated in buffer A containing EDTA (2.5 mM) (Buffer B). The column was washed with 15 ml of buffer B. The aryl propenal double bond reductase was eluted with a linear gradient of NaCl in buffer B (0 to 0.5 M in 80 ml). The active fractions were combined and dialyzed against buffer A for 2 hours.

Anion exchange chromatography. The dialysate was next applied to a Mono Q HR5/5 (Pharmacia) column equilibrated in buffer A. The column was washed with 15 ml of buffer A and the aryl propenal double bond reductase was eluted with a linear NaCl gradient (0 to 1 M in 80 ml). Fractions with aryl propenal double bond reductase activity were combined and pooled.

Amino acid sequencing of aryl propenal double bond reductase—The purified aryl propenal double bond reductase was submitted to SDS-PAGE analysis (4–15% gradient gel, Bio-Rad Laboratories) with the proteins visualized by silver staining. The band corresponding to the aryl propenal double bond reductase was cut and microsequencing (trypsin digestion) was performed at the Harvard Microchemistry Facility (Harvard University) by microcapillary reverse-phase HPLC nano-electrospray tandem mass spectrometry on a Finnigan LCQ quadrupole ion trap mass spectrometer as described in Eng, J. K., et al., *J. Am. Soc. Mass. Spectrom.* 5: 976–989 (1994); Chittum, H. S., et al., *Biochemistry* 37: 10866–10870 (1998); LeRoy, G., et al., *Science* 282: 1900–1904 (1998).

The following three peptide sequences were obtained: ELILVAYANEGPVTDSHLNIR (SEQ ID NO:3), DGSSGDVAVQNLWISVDPYLR (SEQ ID NO:4), and ESDDGLYLPSFPLNQAIR (SEQ ID NO:5).

EXAMPLE 3

This example describes the cloning, from *Pinus taeda*, of a cDNA molecule (SEQ ID NO:1) that encodes a full-length aryl propenal double bond reductase (SEQ ID NO:2), and the expression of the aryl propenal double bond reductase (SEQ ID NO:2) in *E. coli*.

The three peptide sequences (SEQ ID NOS:3, 4 and 5) obtained from *Pinus taeda* aryl propenal double bond reductase, as described in Example 2, were used to screen the GenBank database. All three peptide sequences (SEQ ID NOS:3, 4 and 5) were encoded by an expressed sequence tag (EST), identified as clone 7c5a, obtained from a *Pinus taeda* cDNA library (Allona, I., et al., *Proc. Natl. Acad. Sci. USA*. 95 (16): 9693–9698 (1998) (GenBank accession number AA556927).

In order to obtain a cDNA molecule encoding a full-length aryl propenal double bond reductase from a *P. taeda* cDNA library, a reverse primer (APDBR-IR1, GGA ATC CAG CCC ATG CA (SEQ ID NO:6)) for PCR amplification was designed on the basis of the DNA sequence from EST clone 7c5a. *P. taeda* cDNA library was previously synthesized and stored at 4° C. (Gang, D. R., J. Biol. Chem., Vol. 274, No.11, pp.7516–7527 (1999)). Since cDNAs were cloned into the multiple cloning site flanked by T3 and T7 RNA promoters in Uni-ZAP XR insertion vector, T3 forward primer (SEQ ID NO: 7) and APDBR-IR1 reverse primer (SEQ ID NO:6) were used in a PCR reaction. A PCR product (~590 bp) was obtained and cloned into a pCR®2.1-TOPO vector for sequencing. The resulting pCR®2.1-TOPO construct (APDBR-NT/pCR), containing the N-terminal region of putative aryl propenal double bond reductase, was sequenced completely. The N-terminal primer (APDBR-NT1, AGT GAT TGT ATG TAC AAT TGA GG (SEQ ID NO:8)) was next designed, with APDBR-NT1 (SEQ ID NO:8) and T7 forward primer (SEQ ID NO:9) gave a PCR product (~1.4 Kbp). Four PCR reactions were done to verify that no mutations had been introduced during PCR, and PCR products were cloned into a pCR®2.1-TOPO vector, respectively. Four clones (APDBR/pCR1~APDBR/pCR4) were sequenced completely on both strands to verify that no mutations had been introduced during PCR. The nucleic acid sequence of the aryl propenal double bond reductase cDNA is set forth in SEQ ID NO:1.

Transfer of the aryl propenal double bond reductase cDNA (SEQ ID NO:1) into pGEX-4T-1—A pGEX-4T-1 plasmid, containing the cDNA (SEQ ID NO:1) in frame with *Schistosoma japonicum* glutathion S-transferase, was used (Amersham Pharmacia Biotech). The insertion, containing the putative reductase (SEQ ID NO:2) from *P. taeda*, was prepared by Sticky-end PCR methods (Zeng, G. *BioTechniques* Vol.25. No.2, pp.206–208 (1998)). Four primers were designed to introduce a BamHI site at the start methionine (5'-primer 1: GAT CCA TGG AGC AGA GAG TTC CAA ACA GAG (SEQ ID NO:10) and 5'-primer 2: CAT GGA GCA GAG AGT TCC AAA CAG AG (SEQ ID NO:11) and an EcoRI site in the 3'-end untranslated region (3'-primer 3: CAT CCA GAA TTT ATT TTG GTA GGG G (SEQ ID NO:12) and 3'-primer 4: AAT TCA TCC AGA ATT TAT TTT GGT AGG GG (SEQ ID NO:13).

These four primers were used in PCR with 10 ng of the APDBR/pCR1 containing the *P. taeda* putative reductase cDNA (SEQ ID NO:1). Two PCR products (~1.1K base pairs) were gel purified, combined, denatured and annealed to give the insertion with desired restriction enzyme sites at both ends. The resulting ~1.1 Kb fragment mixtures were directly used for ligation with the pGEX-4T-1 plasmid which had been previously double digested with BamHI and EcoRI. Only the insertion which contained the desired restriction enzyme sites was ligated into pGEX-4T-1 plasmid. The resulting pGEX-4T-1 construct (APDBR/pGEX4T1) was transformed into competent Top10 cells. The APDBR/pGEX4T1, containing the putative aryl propenal double bond reductase cDNA (SEQ ID NO:1), was purified, and the expression region, containing the desired cDNA (SEQ ID NO:1), was sequenced completely on both strands.

Overexpression of the *P. taeda* aryl propenal double bond reductase (SEQ ID NO:2) in *E. coli*—The resulting APDBR/pGEX4T1 plasmid was transformed into the competent Epicurian Coli® BL21-CodonPlus™(DE3)-RIL cells for expression. Expression of the putative reductase (SEQ ID NO:2) was achieved by inoculating 1 liter of LB broth, supplemented with 50 mg/L carbenicillin, with 4 ml of an overnight grown 10 ml culture in the same medium. The cells were then allowed to grow at 37° C. with shaking at 250 rpm until a density of $OD_{600}=0.5$ was reached, at which point the growth conditions were changed to 20° C. Production of the reductase (SEQ ID NO:2) was induced by the addition of isopropyl β-D-thiogalactopyranoside to 1 mM final concentration. The cells were allowed to grow for 21 hours, and harvested by centrifugation for 30 min at 3000× g in 6×250-ml centrifuge bottles, with the pellets stored at −80° C. After cell lysis in phosphate-buffered saline (140 mM NaCl, 2.7 mM KCl, 10 mM $K_2HPO_4$, 1.8 mM $KH_2PO_4$) containing 5 mM DTT, the protein was purified over glutathion-Sepharose 4B resin according to Pharmacia's instructions. The N-terminal glutathione S-transferase fusion was then removed from 26 mg of purified protein by cleavage at 22° C. for 12 hrs with 250 units of thrombin (Amersham Pharmacia Biotech) followed by another glutathion-Sepharose 4B resin purification.

Enzyme assays—Each non-radioactive assay (250 μl) consisted of buffer (50 mM Tris-HCl, pH 8.0), substrate (12.5 mM in DMSO, 10 μl), NADPH (25 mM in $H_2O$, 10 μl), and the enzyme preparation (30 μl containing 5 mM DTT). Controls were performed using either denatured enzyme (boiled 96° C., 10 min) or in absence of enzyme. After 1 hour incubation at 30° C. with shaking, the reaction mixture was extracted with EtOAc (500 μl×2) with the EtOAc solubles combined and evaporated to dryness in vacuo. The EtOAc solubles were dissolved in $CH_3CN$ (10 μl) and then in 3% AcOH (90 μl), and subjected to reverse-phase HPLC with UV detection (280 nm).

Radioactive assays were performed in the same way as the non-radioactive assay with the following exceptions: the reaction was initiated by addition of [4S-$^3$H] or [4R-$^3$H] NADPH (25 mM in $H_2O$, 666.7 kBq 10 μl). The EtOAc solubles were reconstituted in $CH_3CN/H_2O$ and subjected to reverse-phase HPLC as described above with 0.5 ml fractions collected and an aliquot (100 μl) of each removed for scintillation counting to determine the level of incorporation of $^3$H into the products.

Reversed phase HPLC separation of substrates and products—Separation of dehydrodiconiferyl alcohol (DDC), dihydrodehydrodiconiferyl alcohol (DDDC), dehydrodiconiferyl aldehyde (DDCA), dihydrodehydrodiconiferyl aldehyde (DDDCA) coniferyl alcohol (CA), dihydroconiferyl alcohol (DCA), coniferyl aldehyde (CAL), and dihydroconiferyl aldehyde (DCAL) was carried out using a reverse-phase column (Symmetry Shield $RP_8$, 3.9×150 mm, Waters) as follows: $CH_3CN$-3% AcOH in $H_2O$ (1:9) from 0 to 5 min, then linear gradient to 1:3 between 5 to 30 min, and finally linear gradient to 100% $CH_3CN$ over 25 min, at a flow rate of 1 ml/min.

This experiment shows that the expressed aryl propenal double bond reductase (SEQ ID NO:2) was enzymatically active.

EXAMPLE 4

This example describes a representative hybridization protocol that can be used to identify nucleic acid molecules of the invention that hybridize to the nucleic acid molecule consisting of the nucleic acid sequence set forth in SEQ ID NO:1, or to the complement of the nucleic acid molecule consisting of the nucleic acid sequence set forth in SEQ ID NO:1, under defined hybridization conditions.

Hybridization solution should preferably be prepared and filtered through a 0.45-micron disposable cellulose acetate filter. The composition of the hybridization solution is 6×SSC, 5× Denhardt's reagent, 0.5% sodium dodecyl sulfate (SDS), 100 μg/ml denatured, fragmented salmon sperm DNA. When $^{32}$P-labeled cDNA or RNA is used as a probe, poly(A)$^+$ RNA at a concentration of 1 μg/ml may be included in the hybridization solution to prevent the probe from binding to T-rich sequences that are found fairly commonly in eukaryotic DNA.

Float the nitrocellulose filter or nylon membrane containing the target DNA on the surface of a tray of 6×SSC until it becomes thoroughly wetted from beneath. Submerge the filter for 2 minutes. Slip the wet filter into a heat-sealable bag. Add 0.2 ml of hybridization solution for each square centimeter of nitrocellulose filter or nylon membrane.

Squeeze as much air as possible from the bag. Seal the open end of the bag with a heat sealer. Incubate the bag for 1–2 hours submerged at the desired temperature (typically no higher than the hybridization temperature). It is desirable to agitate the bag.

If the radiolabeled probe is double-stranded, denature it by heating for 5 minutes at 100° C. Single-stranded probe need not be denatured. Chill the denatured probe rapidly in ice water. Ideally, probe having a specific activity of $10^9$ cpm/μg, or greater, should be used. Hybridization is carried out for the desired time period at 50° C., typically using 1–2 μg/ml radiolabeled probe.

Working quickly, remove the bag containing the filter from the water bath. Open the bag by cutting off one corner with scissors. Add the denatured probe to the hybridization solution, and then squeeze as much air as possible from the bag. Reseal the bag with the heat sealer so that as few bubbles as possible are trapped in the bag. To avoid radioactive contamination of the water bath, the resealed bag should be sealed inside a second, noncontaminated bag.

Incubate the bag submerged in a water bath for the required period of hybridization (for example, 16 hours) at 50° C. Wearing gloves, remove the bag from the water bath and immediately cut off one corner. Pour out the hybridization solution into a container suitable for disposal, and then cut the bag along the length of three sides. Remove the filter and immediately submerge it in a tray containing several hundred milliliters of 2×SSC and 0.5% SDS at room temperature (no higher than 25° C.). The filter should not be allowed to dry out at any stage during the washing procedure.

After 5 minutes, transfer the filter to a fresh tray containing several hundred milliliters of 2×SSC and 0.1% SDS and incubate for 15 minutes at room temperature with occasional gentle agitation. The filter should then be washed at the desired stringency, i.e., in the desired concentration of SSC and at the desired temperature. If, for example, nucleic acid molecules that hybridize to the probe at a temperature of 55° C. in 1×SSC are sought, then the filter is washed in 1×SSC at 55° C., i.e., nucleic acid molecules that do not hybridize to the probe under conditions of 1×SSC at 55° C. are washed off. Washing is typically done for one hour with several changes of washing solution. Those of ordinary skill in the art will recognize that both the hybridization and wash steps can be conducted at the desired stringency. For example, if nucleic acid molecules that hybridize to the probe at 1×SSC at 55° C. are sought, then hybridization and washing can both be conducted in 1×SSC at 55° C. in accordance with the foregoing protocol.

After washing remove most of the liquid from the filter by placing it on a pad of paper towels. Place the damp filter on a sheet of Saran Wrap. Apply adhesive dot labels marked with radioactive ink to several asymmetric locations on the Saran Wrap. These markers serve to align the autoradiograph with the filter. Cover the labels with Scotch Tape. This prevents contamination of the film holder or intensifying screen with the radioactive ink. Radioactive ink is made by mixing a small amount of $^{32}$P with waterproof black drawing ink. Use a fiber-tip pen to apply ink to the adhesive labels.

Cover the filter with a second sheet of Saran Wrap, and expose the filter to X-ray film (Kodak XAR-2 or equivalent) to obtain an autoradiographic image. The exposure time should be determined empirically.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated nucleic acid molecule that:
   (a) encodes an aryl propenal double bond reductase; and
   (b) hybridizes to the complement of SEQ ID NO: 1 under hybridization conditions of 1×SSC, 65° C. for one hour.

2. An isolated nucleic acid molecule of claim 1 that hybridizes to the complement of SEQ ID NO: 1 under conditions of 1×SSC, 65° C. for one hour.

3. An isolated nucleic acid molecule of claim 1 wherein said isolated nucleic acid molecule is a cDNA molecule.

4. An isolated nucleic acid molecule of claim 1, wherein said isolated nucleic acid molecule consists of the nucleic acid sequence set forth in SEQ ID NO:1.

5. An isolated nucleic acid molecule that encodes an aryl propenal double bond reductase that is at least 70% identical to the aryl propenal double bond reductase consisting of the amino acid sequence set forth in SEQ ID NO:2.

6. An isolated nucleic acid molecule of claim 5 wherein said aryl propenal double bond reductase is at least 80% identical to the aryl propenal double bond reductase consisting of the amino acid sequence set forth in SEQ ID NO:2.

7. An isolated nucleic acid molecule of claim 5 wherein said aryl propenal double bond reductase is at least 90% identical to the aryl propenal double bond reductase consisting of the amino acid sequence set forth in SEQ ID NO:2.

8. An isolated nucleic acid molecule of claim 5 that encodes an aryl propenal double bond reductase consisting of the amino acid sequence set forth in SEQ ID NO:2.

9. A vector comprising a nucleic acid molecule that:

(a) encodes an aryl propenal double bond reductase; and (b) hybridizes to the complement of SEQ ID NO:1 under hybridization conditions of 1×SSC, 55° C. for one hour.

10. A vector of claim 9 wherein said nucleic acid molecule hybridizes to the complement of SEQ ID NO: 1 under hybridization conditions of 1×SSC, 65° C. for one hour.

11. A vector of claim 9 wherein said nucleic acid molecule consists of the nucleic acid sequence set forth in SEQ ID NO:2.

12. A vector comprising a nucleic acid molecule that encodes an aryl propenal double bond reductase that is at least 70% identical to the aryl propenal double bond reductase consisting of the amino acid sequence set forth in SEQ ID NO: 2.

13. A host cell comprising a vector of claim 9.

14. A host cell of claim 13 wherein said host cell is a plant cell.

15. A host cell comprising a vector of claim 12.

16. A host cell of claim 15 wherein said host cell is a plant cell.

17. A method of enhancing the level of aryl propenal double bond reductase in a plant, the method comprising the steps of:

(a) introducing into a plant an expression vector comprising a nucleic acid molecule that:

(1) encodes an aryl propenal double bond reductase;

(2) hybridizes to the complement of SEQ ID NO: 1 under hybridization conditions of 1×SSC, 65° C. for one hour; and (b) expressing the aryl propenal double bond reductase within the plant.

18. The method of claim 17 wherein the plant is a gymnosperm.

19. The method of claim 17 wherein said aryl propenal double bond reductase is at least 70% identical to the aryl propenal double bond reductase consisting of the sequence set forth in SEQ ID NO: 2.

20. A method of inhibiting the expression of aryl propenal double bond reductase in a plant, the method comprising the steps of:

(a) introducing into a plant an expression vector that comprises a nucleic acid molecule that is in antisense orientation relative to a promoter, the nucleic acid molecule hybridizing to the nucleic acid molecule consisting of the nucleic acid sequence set forth in SEQ ID NO: 1 under hybridization conditions of 1×SSC, 65° C. for one hour; and (b) transcriptionally expressing the nucleic acid molecule in the plant.

21. The method of claim 20 wherein the plant is a gymnosperm.

22. The method of claim 20 wherein the nucleic acid molecule hybridizes to the nucleic acid molecule consisting of the nucleic acid sequence set forth in SEQ ID NO: 1 under conditions of 1×SSC at 65° C. for one hour.

\* \* \* \* \*

UNITED STATES PATENT AND TRADEMARK OFFICE
CERTIFICATE OF CORRECTION

PATENT NO. : 6,703,229 B2
DATED : March 9, 2004
INVENTOR(S) : H. Kasahara et al.

It is certified that error appears in the above-identified patent and that said Letters Patent is hereby corrected as shown below:

Title page,
Item [75], Inventors, "Wako (JP);" should read -- Wako-shi (JP); --
Item [56], References Cited, OTHER PUBLICATIONS, "Nucleic Acid Sequence", reference, after "*EMBL*" delete ","

Column 5,
Lines 33-34, "Molecular Cloning, A Laboratory Manual" should read -- *Molecular Cloning, A Laboratory Manual* --
Line 35, "eds" should read -- eds. --
Line 50, "art: For" should read -- art. For --

Column 6,
Line 38, "Agrobacterium" should read -- *Agrobacterium* --
Line 56, "20(17):1425(1992);" should read -- 20(17):1425 (1992); --
Line 64, "Agrobacterium-mediated" should read -- *Agrobacterium*-mediated --

Column 7,
Line 13, "Agrobacterium" should read -- *Agrobacterium* --
Line 51, "(1984);" should read -- (1984)). --
Lines 61-62, "5,599,
           670," should not break Column 8,
Line 19, "H. -Q.," should read -- H.-Q., --
Lines 28-29, "5,416,
           011;" should not break
Lines 32-33, "5,463,
           174" should not break
Lines 55-56, "Genetic Engineering, Principles and Methods" should read
-- *Genetic Engineering, Principles and Methods* --

Column 9,
Line 3, "encoding an aryl propenal double bond reductases" should read -- encoding an aryl propenal double bond reductase --

UNITED STATES PATENT AND TRADEMARK OFFICE
CERTIFICATE OF CORRECTION

PATENT NO. : 6,703,229 B2
DATED : March 9, 2004
INVENTOR(S) : H. Kasahara et al.

It is certified that error appears in the above-identified patent and that said Letters Patent is hereby corrected as shown below:

Column 10,
Line 20, "Saccharomyces." should read -- *Saccharomyces.* --
Line 31, "20(17):1425(1992);" should read -- (17):1425 (1992); --
Line 66, "Pseudomonas" should read -- *Pseudomonas* --

Column 11,
Line 6, "Genetic Engineering, Principles and Methods," should read -- *Genetic Engineering, Principles and Methods,* --

Column 12,
Line 63, "in three ways;" should read -- in three ways: --

Column 13,
Line 42, "5,723,
            761," should not break
Line 66, after "construct" delete ","

Column 14,
Line 23, "ps. 121-147," should read -- pp. 121-147, --
Line 26, , "Agrobacterium-mediated" should read -- *Agrobacterium*-mediated --
Lines 30 and 31, "Picea." should read -- *Picea.* --
Line 32, "Molecular Biology of Woody Plants" should read -- *Molecular Biology of Woody Plants* --
Line 50, after "described below" insert -- , --
Line 53, "*volumes, 3rd Ed.*" should read -- "volumes, 3rd Ed. --
Line 55, "*volumes*" should read -- volumes --
Line 66, after "cells were" insert -- obtained --

Column 15,
Line 8, after "Inc." insert -- , --
Line 16, after "previously described" delete "in"
Lines 16 and 19, "J. Biol. Chem." should read -- *J. Biol. Chem.* --
Line 18, after "as described" delete "in"
Lnes 50-51, "performed on Millenium™ (Waters Inc.) instrument using" should read -- performed on a Millenium™ (Waters Inc.) instrument using --

UNITED STATES PATENT AND TRADEMARK OFFICE
CERTIFICATE OF CORRECTION

PATENT NO.    : 6,703,229 B2
DATED         : March 9, 2004
INVENTOR(S)   : H. Kasahara et al.

It is certified that error appears in the above-identified patent and that said Letters Patent is hereby corrected as shown below:

Column 17,
Line 12, "J. Biol. Chem.," should read -- *J. Biol. Chem.*, --
Line 44, after "NO:11)" insert -- ) --
Line 48, after "NO:13)" insert -- ) --

Column 27,
Line 62, "65°C" should read -- 55°C --

Column 30,
Lines 3 and 22, "65°C" should read -- 55°C --

Signed and Sealed this

Twenty-first Day of September, 2004

JON W. DUDAS
*Director of the United States Patent and Trademark Office*